(12) United States Patent
Weiguny et al.

(10) Patent No.: US 7,169,732 B2
(45) Date of Patent: Jan. 30, 2007

(54) CATALYST-PRECURSOR FOR THE PRODUCTION OF MALEIC ACID ANHYDRIDE AND METHOD FOR THE PRODUCTION THEREOF

(75) Inventors: Jens Weiguny, Shanghai (CN); Sebastian Storck, Mannheim (DE); Mark Duda, Ludwigshafen (DE); Cornelia Dobner, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 231 days.

(21) Appl. No.: 10/507,610

(22) PCT Filed: Mar. 12, 2003

(86) PCT No.: PCT/EP03/02506

§ 371 (c)(1),
(2), (4) Date: Sep. 14, 2004

(87) PCT Pub. No.: WO03/078058

PCT Pub. Date: Sep. 25, 2003

(65) Prior Publication Data

US 2005/0222436 A1    Oct. 6, 2005

(30) Foreign Application Priority Data

Mar. 15, 2002 (DE) ................. 102 11 445

(51) Int. Cl.
*B01J 27/18* (2006.01)
*C07D 307/60* (2006.01)

(52) U.S. Cl. ........................ 502/209; 549/259
(58) Field of Classification Search ........... 549/259; 502/209
See application file for complete search history.

(56) References Cited

U.S. PATENT DOCUMENTS

| | | |
|---|---|---|
| 4,670,415 A | 6/1987 | Keppel et al. |
| 4,795,818 A | 1/1989 | Becker et al. |
| 4,933,312 A | 6/1990 | Haddad et al. |
| 5,137,860 A | 8/1992 | Ebner et al. |
| 5,158,923 A | 10/1992 | Barone |
| 5,168,090 A | 12/1992 | Ebner et al. |
| 5,296,436 A | 3/1994 | Bortinger |
| 5,364,824 A | 11/1994 | Andrews et al. |

FOREIGN PATENT DOCUMENTS

| | | |
|---|---|---|
| EP | 56 183 | 7/1982 |
| EP | 520 972 | 12/1992 |
| WO | 93/01155 | 1/1993 |
| WO | 95/26817 | 10/1995 |
| WO | 95/29006 | 11/1995 |
| WO | 97/12674 | 4/1997 |
| WO | 00/72963 | 12/2000 |
| WO | 02/68245 | 9/2001 |

OTHER PUBLICATIONS

Ullmann's Encyclopedia of Industrial Chem., 6th Ed., 2000 electronic release, Chapter "Malelic and Fumaric Acids", Maleic Anhydride Production Kubias et al., 72(3), 2000, pp. 249-251.

*Primary Examiner*—Bernard Dentz
(74) *Attorney, Agent, or Firm*—Novak Druce & Quigg LLP

(57) ABSTRACT

A process for preparing a vanadium, phosphorus, and oxygen catalyst precursor for preparing maleic anhydride by heterogeneously catalyzed gas-phase oxidation of a hydrocarbon having at least four carbon atoms, which comprises (a) reacting vanadium pentoxide with from 102 to 110% strength phosphoric acid in the presence of a primary or secondary, noncyclic or cyclic, unbranched or branched, saturated alcohol having from 3 to 6 carbon atoms in a temperature range from 80 to 160° C.;

(b) isolating the precipitate formed;

(c) setting an organic carbon content of $\leq 1.1\%$ by weight in the isolated precipitate by heat treatment in a temperature range from 250 to 350° C., the heat-treated product, following the addition of 3.0% by weight of graphite, giving a powder X-ray diffraction diagram which in the 2θ region features a ratio of the height of the peak of any pyrophosphate phase present at 28.5° to the height of the peak due to the graphite at 26.6° of $\leq 0.1$; and (d) shaping the heat-treated product obtained from step (c) into particles having an averaged diameter of at least 2 mm;

a catalyst precursor obtainable from this process; a process for preparing a catalyst from the catalyst precursor; a catalyst obtainable from that process; and also a process for preparing maleic anhydride over that catalyst.

10 Claims, 5 Drawing Sheets

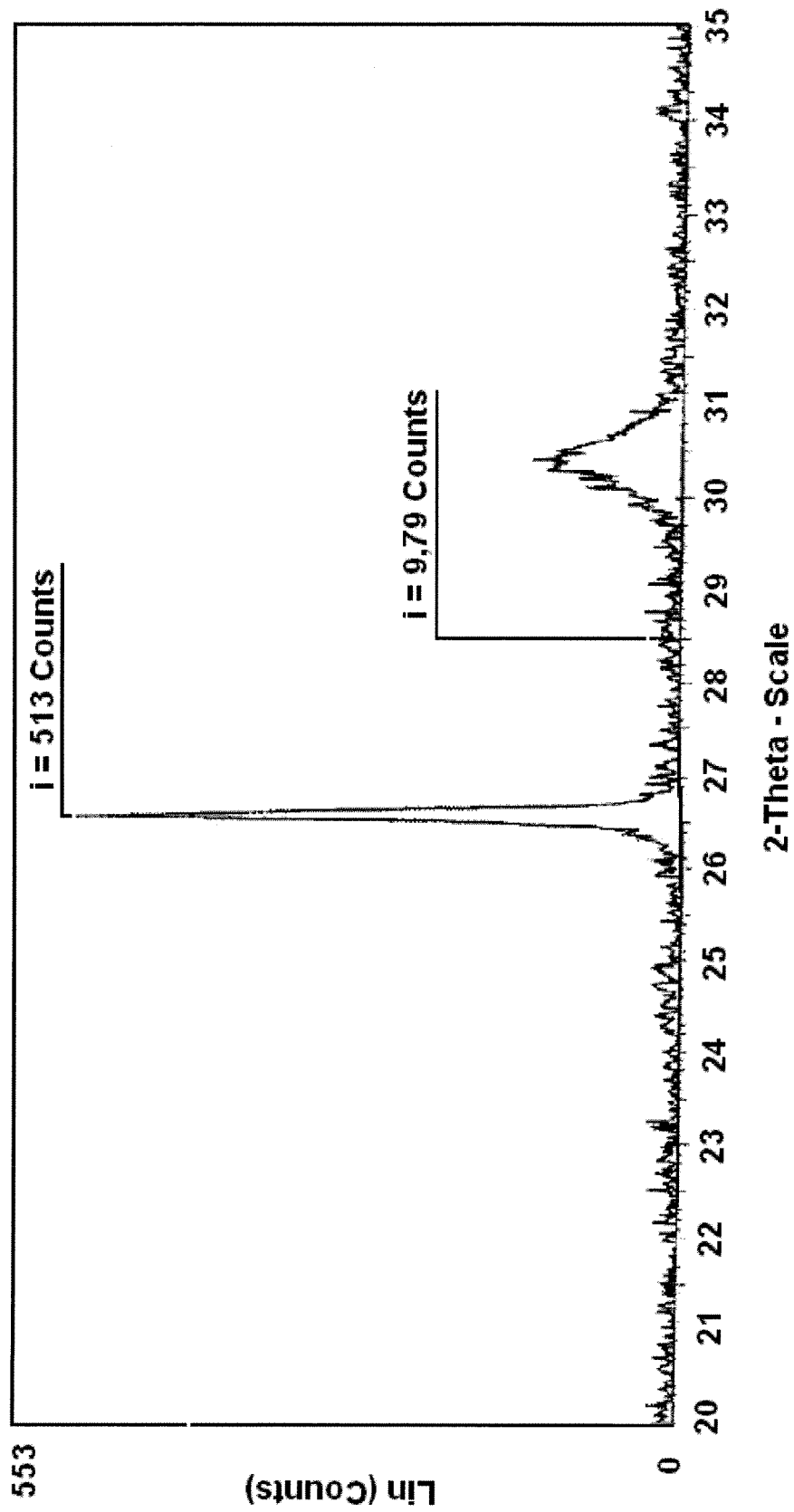
Fig. 1: Background-corrected XRD diagram of a representative sample of the catalyst precursor from example 2.2, heat-treated in the muffle furnace, following addition of 3.0% by weight of graphite.

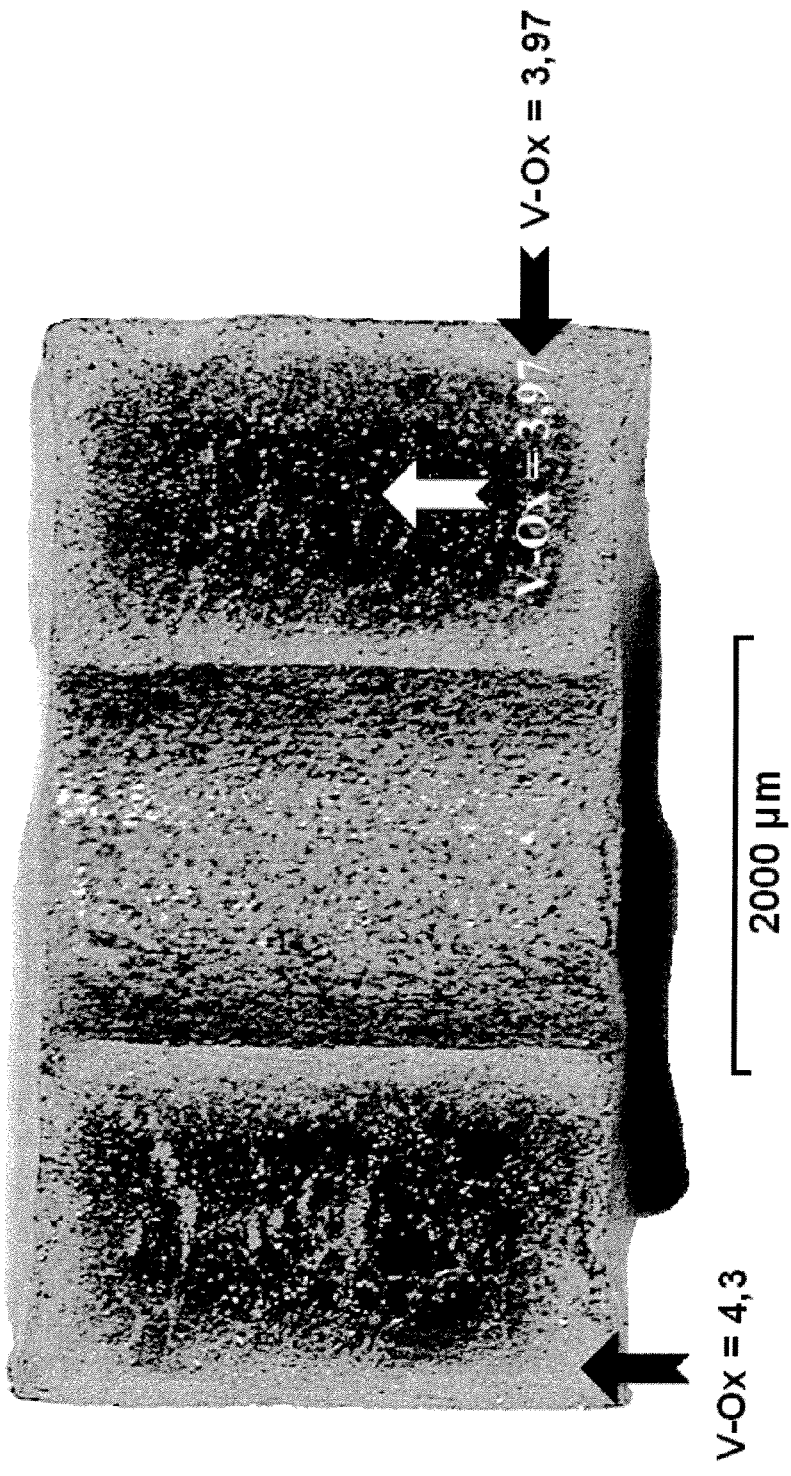
Fig. 2: Light micrograph of the catalyst from example 2.1 heat-treated in the muffle furnace at 250°C and then tableted and calcined (comparative example). The duplicate arrow signifying "V-Ox = 3,97" is provided merely to clarify the difficult to read white text and white arrow, which were originally placed overtop of the light micrograph.

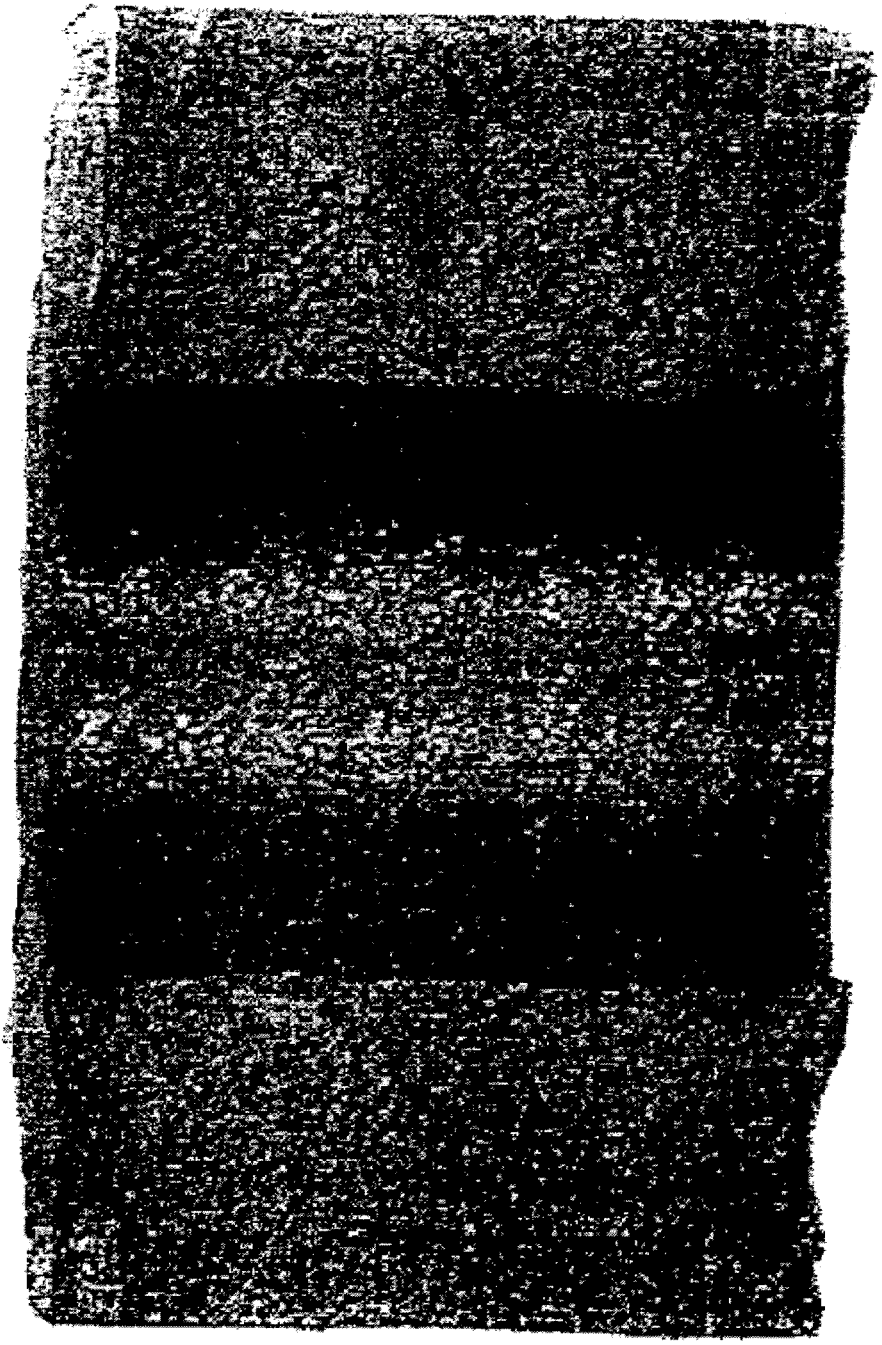
Fig. 3: Light micrograph of the catalyst from example 2.2 heat-treated in the muffle furnace at 300°C and then tableted and calcined.

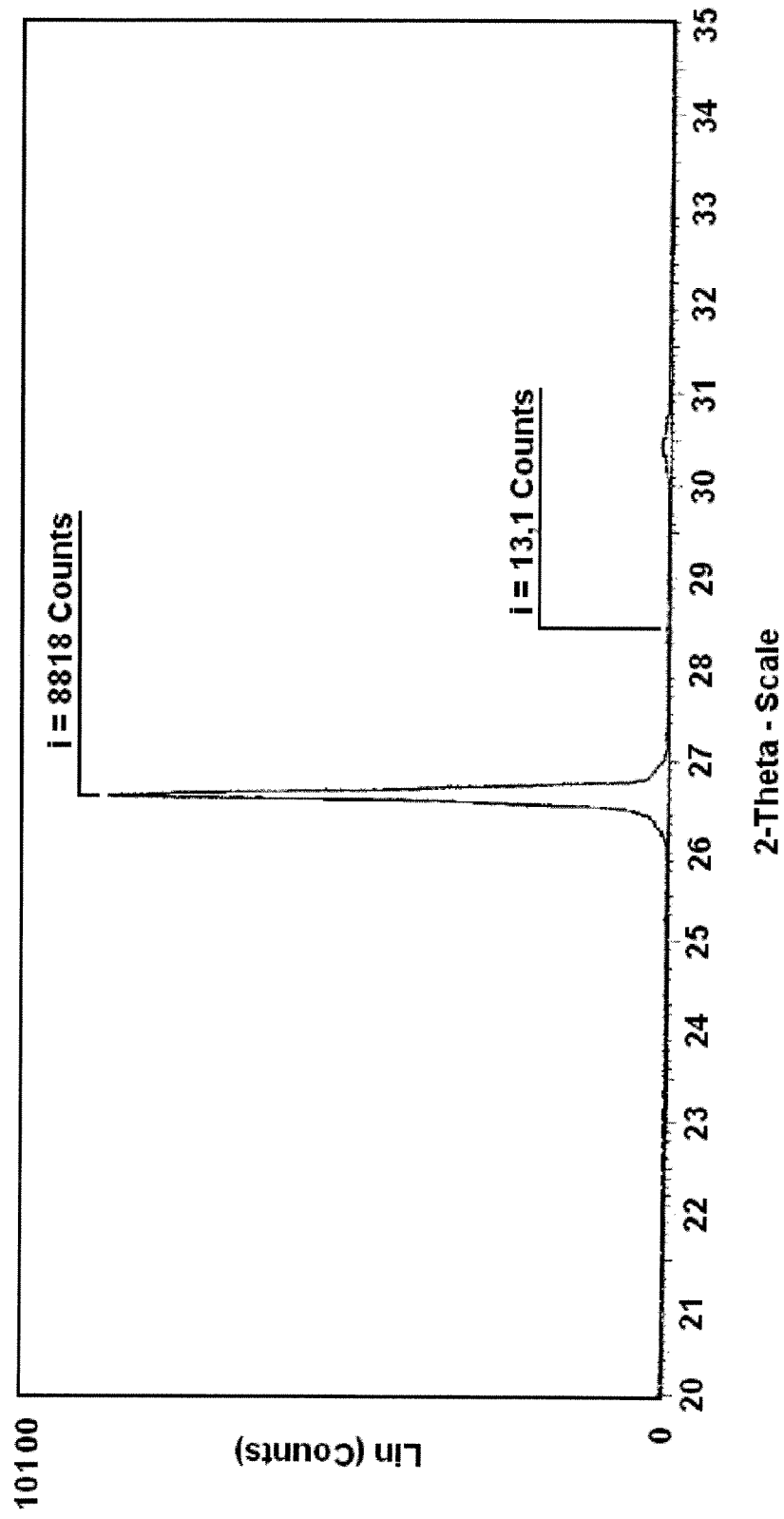
Fig. 4: Background-corrected XRD diagram of a representative sample of the catalyst precursor from example 4.4, heat-treated in the rotary tube, following addition of 3.0% by weight of graphite.

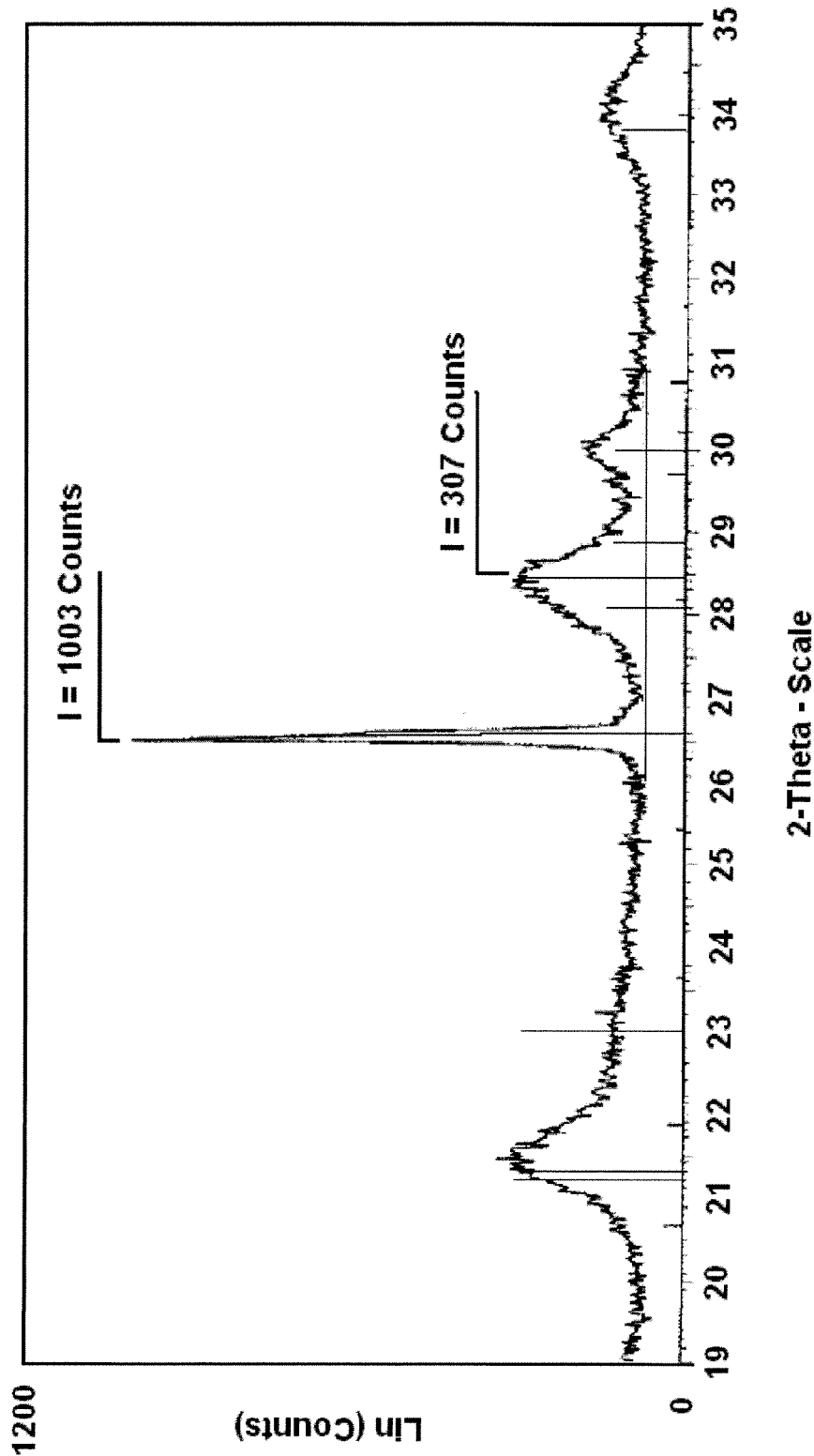
Fig. 5: XRD diagram of the catalyst precursor from example 6, heat-treated at 400°C, following addition of 3.0% by weight of graphite.

CATALYST-PRECURSOR FOR THE PRODUCTION OF MALEIC ACID ANHYDRIDE AND METHOD FOR THE PRODUCTION THEREOF

This application is a 371 of PCT/EP03/02506 filed Mar. 12, 2003.

The present invention relates to a vanadium, phosphorus, and oxygen catalyst precursor and also to a process for its preparation for preparing maleic anhydride by heterogeneously catalyzed gas-phase oxidation of a hydrocarbon having at least four carbon atoms.

The present invention further relates to a vanadium-phosphorus-oxygen catalyst and to a process for preparing it using the catalyst precursor of the invention.

The present invention additionally relates to a process for preparing maleic anhydride by heterogeneously catalyzed gas-phase oxidation of a hydrocarbon having at least four carbon atoms using the catalyst of the invention.

Maleic anhydride is an important intermediate in the synthesis of γ-butyrolactone, tetrahydrofuran, and 1,4-butanediol, which in turn are used as solvents or are processed further, for example, to polymers, such as polytetrahydrofuran or polyvinylpyrrolidone.

The preparation of maleic anhydride by oxidizing hydrocarbons such as n-butane, n-butenes or benzene over suitable catalysts is well established. It is generally carried out using vanadium-phosphorus-oxygen catalysts (known as VPO catalysts) (see Ullmann's Encyclopedia of Industrial Chemistry, $6^{th}$ edition, 2000 electronic release, Chapter "MALEIC AND FUMARIC ACIDS, Maleic Anhydride—Production").

The vanadium-phosphorus-oxygen catalysts widely employed are generally prepared as follows:

(1) Synthesis of a vanadyl phosphate hemihydrate precursor ($VOHPO_4 \cdot \frac{1}{2} H_2O$) from a pentavalent vanadium compound (e.g., $V_2O_5$), a pentavalent or trivalent phosphorus compound (e.g., orthophosphoric and/or pyrophosphoric acid, phosphates or phosphorous acid), and a reductive alcohol (e.g., isobutanol), isolation of the precipitate, and drying, with shaping where appropriate (tableting for example); and (2) preactivation to give vanadyl pyrophosphate (($VO)_2P_2O_7$) by calcination.

Owing to the use of a reductive alcohol as reductant, several percent by weight of organic compounds generally remain included in the resultant precursor precipitate, and cannot be removed even by painstaking washing. During the subsequent preparation of the catalyst, and especially during calcining, these organic compounds exert a negative effect on the catalytic properties of the catalyst. For instance, during the later calcining operation, there is a risk of these included organic compounds evaporating and/or undergoing thermal decomposition to form gaseous components which may lead to an increase in pressure inside the catalyst structure and hence to its destruction. This deleterious effect is particularly strongly pronounced when calcining is carried out under oxidative conditions, since the formation of the oxidized degradation products, such as carbon monoxide or carbon dioxide, produces a substantially greater volume of gas. Moreover, the oxidation of these organic compounds produces very large quantities of heat locally, which may lead to thermal damage to the catalyst.

Furthermore, the included organic compounds possess a significant influence on the local oxidation state of the vanadium. Thus in Chemie Ingenieur Technik 72(3), 2000, pages 249 to 251 B. Kubias et al. demonstrate the reductive effect of organic carbon in the anaerobic calcination (under nonoxidative conditions) of a vanadyl hydrogen phosphate hemihydrate precursor obtained from solution in isobutanol. In the example given, anaerobic calcination produces an average oxidation state of the vanadium of 3.1 whereas aerobic calcination (under oxidative conditions) produces an average oxidation state of the vanadium of approximately 4.

EP-A 0 520 972 describes the preparation of a vanadyl hydrogen phosphate hemihydrate precursor by reacting vanadium pentoxide with phosphoric acid in an organic medium, such as a primary or secondary alcohol, for example. The amount of adhering and/or included organic compounds is said to be up to 40% by weight, the citation teaching that 8-hour drying at 150° C. leads to an amount of approximately 25% by weight and 4-hour drying (heat treatment) at 250° C. leads to an amount of approximately 2% by weight.

Example 1 of EP-A 0 520 972 describes the preparation of the precursor by reacting vanadium pentoxide with 105.7% strength phosphoric acid in the presence of oxalic acid in isobutanol as the reductive organic medium, with heating under reflux, followed by decanting the supernatant solution, drying of the remaining slurry at from 100 to 150° C., and subsequent five-hour heat treatment at from 250 to 260° C. The catalyst precursor obtained was subsequently mixed with graphite, tableted, and calcined under a variety of calcining conditions to give the finished catalyst comprising vanadyl pyrophosphate. A particular disadvantage of the preparation procedure it describes is the high level of adhering and/or included organic compounds in the precursor, which can be attributed (i) to the use of oxalic acid, (ii) to the decanting of the supernatant solution and evaporative concentration of the remaining slurry, and (iii) to the heat treatment conditions selected.

Example 2 of EP-A 0 520 972 describes the preparation of the precursor by reacting vanadium pentoxide with 100% strength phosphoric acid in the presence of isobutanol as the reductive organic medium with heating under reflux, filtration, washing, and drying at 145° C. The resulting catalyst precursor was subsequently calcined in air at 400° C. for one hour, mixed with graphite, and tableted to give the finished catalyst. As a result of the selected calcining temperature of 400° C., the phase transformation to give vanadyl pyrophosphate has already taken place in the powderous state prior to tableting.

WO 00/72963 teaches the preparation of a vanadyl hydrogen phosphate hemihydrate precursor by reacting vanadium pentoxide with orthophosphoric acid in the presence of isobutanol and a polyol (a diol for example), with the resultant precipitate being subsequently filtered, washed, dried at from 120 to 200° C., heat-treated in air at 300° C. for 3 hours, tableted, and calcined at a temperature of up to 600° C. in order to convert it into the catalytically active form. Following three-hour heat treatment at 300° C., the precursor prepared by these measures has a carbon content of from 0.7 to 3% by weight. The best catalytic properties are achieved with catalysts which have been prepared in accordance with the teaching of the cited document, using orthophosphoric acid in the presence of isobutanol and a polyol, and for which the carbon content of the precursor following the stated three-hour heat treatment at 300° C. is from 0.8 to 1.5% by weight. The yield of maleic anhydride achieved when using such a catalyst at 400° C. was approximately 30 to 45%. Contrastingly, a catalyst precipitated by reacting vanadium pentoxide with orthophosphoric acid in the presence of isobutanol, whose precursor already has a relatively low carbon content of 0.6% by weight following five-hour drying at 125° C., exhibits a far lower yield of maleic anhydride, of approximately 17% at 400° C.

The remarks in WO 00/72963 show that a low carbon content in the precursor is not a sufficient criterion for the obtention of an active and selective catalyst. The preparation process it proposes has the disadvantage of using a further organic component and also of a relatively poor performance by the catalyst which can be obtained, whereby even at a reaction temperature of 400° C. a maleic anhydride yield of only 30 to 45% is achieved.

EP-A 0 056 183 teaches the preparation of a vanadyl hydrogen phosphate hemihydrate precursor by reducing vanadium pentoxide in a reductive liquid medium, reacting the resultant intermediate with a mixture of 45 to 90% orthophosphoric, 10 to 50% pyrophosphoric, and 0 to 10% triphosphoric and polyphosphoric acid, separating off the precipitate, and subjecting it to drying and calcination. Examples 1 to 7 describe the preparation of the precursor by reacting vanadium pentoxide with a mixture of 49% orthophosphoric, 42% pyrophosphoric, 8% triphosphoric, and 1% polyphosphoric acid (corresponding approximately to 105% strength phosphoric acid) in the presence of isobutanol with heating under reflux, filtration, and drying at 150° C. The catalyst precursor obtained was then calcined in air at 400° C. for one hour, mixed with graphite, and tableted to give the finished catalyst. As a result of the chosen calcination temperature of 400° C., phase transformation to give the vanadyl pyrophosphate has already taken place in the powderous state prior to tableting.

It is an object of the present invention to find a process for preparing a vanadium, phosphorus, and oxygen catalyst precursor for preparing maleic anhydride by heterogeneously catalyzed gas-phase oxidation of a hydrocarbon having at least four carbon atoms that no longer possesses the disadvantages set out above, is easy to carry out industrially, and, following preactivation, which should likewise be easy to carry out industrially, gives a particulate catalyst featuring a substantially homogeneous vanadium oxidation state both within the individual catalyst particles and between the different catalyst particles, and which possesses high activity and high selectivity.

We have found that this object is achieved by a process for preparing a vanadium, phosphorus, and oxygen catalyst precursor for preparing maleic anhydride by heterogeneously catalyzed gas-phase oxidation of a hydrocarbon having at least four carbon atoms, which comprises
(a) reacting vanadium pentoxide with from 102 to 110% strength phosphoric acid in the presence of a primary or secondary, noncyclic or cyclic, unbranched or branched, saturated alcohol having from 3 to 6 carbon atoms in a temperature range from 80 to 160° C.;
(b) isolating the precipitate formed;
(c) setting an organic carbon content of $\leqq 1.1\%$ by weight in the isolated precipitate by heat treatment in a temperature range from 250 to 350° C., the heat-treated product, following the addition of 3.0% by weight of graphite as internal standard and using CuKα radiation ($\lambda=1.54 \cdot 10^{-10}$ m), giving a powder X-ray diffraction diagram which in the 2θ region features a ratio of the height of the peak of any pyrophosphate phase present at 28.5° to the height of the peak due to the graphite at 26.6° of $\leqq 0.1$; and
(d) shaping the heat-treated product obtained from step (c) into particles having an averaged diameter of at least 2 mm.

Essential to the process of the invention are:
the use of phosphoric acid with a strength of from 102 to 110%,
the use of a primary or secondary, noncyclic or cyclic, unbranched or branched, saturated alcohol having from 3 to 6 carbon atoms,
the setting of an organic carbon content of $\leqq 1.1\%$ by weight by heat treatment under appropriate conditions with substantial avoidance of the formation of a pyrophosphate phase, and
the shaping of the heat-treated, substantially pyrophosphatephase-free product.

Steps (a) to (d) above are illustrated in more detail below:

Step (a)

The phosphoric acid for use in the process of the invention possesses an arithmetic $H_3PO_4$ content of from 102 to 110% by weight. This is expressed for simplification as phosphoric acid with a strength of from 102 to 110%. The 102 to 110% strength phosphoric acid is a mixture comprising orthophosphoric acid ($H_3PO_4$), pyrophosphoric acid ($H_4P_2O_7$), and polyphosphoric acids with the formula $H_{n+2}P_nO_{3n+1}$ with $n \geqq 23$. For the process of the invention it is preferred to use phosphoric acid with a strength of from 102 to 108%, with particular preference from 102 to 106%, and with very particular preference from 104 to 106%. The phosphoric acid for use is generally prepared by introducing phosphorus pentoxide into water or aqueous phosphoric acid with a strength, for example, of from 85 to 100%.

As compared with the use of phosphoric acid at a lower concentration, in particular phosphoric acid with a strength of from 85 to 100%, and also solid orthophosphoric acid, the inventive measure of using 102 to 110% strength phosphoric acid, in combination with the other inventive measures, leads surprisingly to the formation of a catalyst precursor which under comparable conditions gives a catalyst which possesses a higher activity and a higher selectivity for maleic anhydride and provides a higher yield of maleic anhydride. As a result of the higher activity, it is possible when using the catalyst to set—for example—a lower reaction temperature.

The reductive component used in the process of the invention is a primary or secondary, noncyclic or cyclic, unbranched or branched, saturated alcohol having from 3 to 6 carbon atoms or a mixture of such alcohols. For the process of the invention it is preferred to use a primary or secondary, unbranched or branched, $C_3$ to $C_6$ alkanol or to use cyclopentanol or cyclohexanol. Suitable alcohols include n-propanol (1-propanol), isopropanol (2-propanol), n-butanol (1-butanol), sec-butanol (2-butanol), isobutanol (2-methyl-1-propanol), 1-pentanol, 2-pentanol, 3-pentanol, 2-methyl-1-butanol, 3-methyl-1-butanol, 3-methyl-2-butanol, 2,2-dimethyl-1-propanol, 1-hexanol, 2-hexanol, 3-hexanol, 2-methyl-1-hexanol, 3-methyl-1-pentanol, 4-methyl-1-pentanol, 3-methyl-2-pentanol, 4-methyl-2-pentanol, 2,2-dimethyl-1-butanol, 2,3-dimethyl-1-butanol, 3,3-dimethyl-1-butanol, 3,3-dimethyl-2-butanol, cyclopentanol, cyclohexanol, and mixtures thereof. Used with particular preference are primary, unbranched or branched, $C_3$ to $C_5$ alkanols and also cyclohexanol. Very particular preference is given to n-propanol (1-propanol), n-butanol (1-butanol), isobutanol (2-methyl-1-propanol), 1-pentanol, 2-methyl-1-butanol, 3-methyl-1-butanol, and cyclohexanol, especially isobutanol.

The inventive measure of using a primary or secondary, noncyclic or cyclic, unbranched or branched, saturated alcohol having from 3 to 6 carbon atoms makes it easy to remove the alkanol and its decomposition products and hence to achieve a low organic carbon content in the heat-treated precipitate. In contrast, for example, reductants such as benzyl alcohol and its decomposition products from the reduction are much more difficult to remove, ultimately implying a disadvantageously high organic carbon content.

Furthermore, in the process of the invention, additional reductive components may be used as well. Examples include ethanol, formic acid, and oxalic acid. The process of the invention is preferably conducted without adding additional reductive components.

The vanadium pentoxide is used preferably in the form of a powder, with particular preference in a particle range from 50 to 500 μm. Where much larger particles are present, the solid is comminuted before being used and is sieved where appropriate. Examples of suitable apparatus are ball mills or planetary mills.

In the preparation of the catalyst precursor it is also possible to add what are known as promoter components. Suitable promoters are the elements of groups 1 to 15 of the Periodic System and also their compounds. Suitable promoters are described, for example, in WO 97/12674 and WO 95/26817 and also in U.S. Pat. Nos. 5,137,860, 5,296,436, 5,158,923 and 4,795,818. Preferred promoters are compounds of the elements cobalt, molybdenum, iron, zinc, hafnium, zirconium, lithium, titanium, chromium, manganese, nickel, copper, boron, silicon, antimony, tin, niobium and bismuth, with particular preference molybdenum, iron, zinc, antimony, bismuth, and lithium. The promoted catalysts may comprise one or more promoters. The promoter components are generally added during step (a), i.e., said reaction of the vanadium pentoxide with from 102 to 110% strength phosphoric acid in the presence of a primary or secondary, noncyclic or cyclic, unbranched or branched, saturated alcohol having from 3 to 6 carbon atoms. The total promoter content of the finished catalyst is generally not more than about 5% by weight, calculated in each case as the oxide.

Where promoted catalyst precursors are prepared by the process of the invention, the promoter is generally added in the form of an organic or inorganic salt during the combination of the vanadium pentoxide, the 102 to 110% strength phosphoric acid, and the primary or secondary, noncyclic or cyclic, unbranched or branched, saturated alcohol having from 3 to 6 carbon atoms. Examples of suitable promoter compounds are the acetates, acetylacetonates, oxalates, oxides, and alkoxides of the aforementioned promoter metals, such as cobalt(II) acetate, cobalt(II) acetylacetonate, cobalt(II) chloride, molybdenum(VI) oxide, molybdenum (III) chloride, iron(III) acetylacetonate, iron(III) chloride, zinc(II) oxide, zinc(II) acetylacetonate, lithium chloride, lithium oxide, bismuth(III) chloride, bismuth(III) ethylhexanoate, nickel(II) ethylhexanoate, nickel(II) oxalate, zirconyl chloride, zirconium(IV) butoxide, silicon(IV) ethoxide, niobium(V) chloride, and niobium(V) oxide. For further details, refer to the aforementioned WO OPI documents and U.S. patents.

In the process of the invention, the combining of the vanadium pentoxide, the 102 to 110% strength phosphoric acid, and the primary or secondary, noncyclic or cyclic, unbranched or branched, saturated alcohol having from 3 to 6 carbon atoms can be accomplished in a variety of ways. For example, said components may be introduced initially or added neat, in diluted form or, in the case of vanadium pentoxide, as a suspension. Dilution or suspension is generally carried out using the primary or secondary, noncyclic or cyclic, unbranched or branched, saturated alcohol having from 3 to 6 carbon atoms.

Said combining is generally carried out in the reaction apparatus suitable for the subsequent reaction—a stirred tank, for example—and with mixing. The components to be combined, in neat, diluted or suspended form, are generally conditioned to a temperature in the range from 0 to 160° C., although the components to be combined may of course possess a different temperature.

Without limitation, a number of variants of the combining operation are described below.

In one variant of said combining, the components are brought together at a temperature in the range from 0 to 50° C. in the reaction apparatus with stirring. In this case the sequence of addition of the individual components is generally unimportant.

In another variant of said combining, a suspension of vanadium pentoxide in a primary or secondary, noncyclic or cyclic, unbranched or branched, saturated alcohol having from 3 to 6 carbon atoms is charged to the reaction apparatus and is then brought preferably to a temperature from 50 to 160° C. and with particular preference from 50 to 100° C. The 102 to 110% strength phosphoric acid, which if desired may have been diluted with a primary or secondary, noncyclic or cyclic, unbranched or branched, saturated alcohol having from 3 to 6 carbon atoms, is then fed into this suspension with stirring. In order to lower the viscosity of the phosphoric acid to be fed in, it may be advantageous to condition it to a temperature in the range from 40 to 100° C.

In a further variant of said combining, as already described for the last-mentioned variant, a suspension of vanadium pentoxide in a primary or secondary, noncyclic or cyclic, unbranched or branched, saturated alcohol having from 3 to 6 carbon atoms is charged to the reaction apparatus and is heated with stirring again to a temperature from 50 to 160° C. In contradistinction to the last-mentioned variant, however, the preferred temperature range is higher, at from 80 to 160° C. Moreover, the system is left under reflux conditions for a period of from about 0.5 hour to several hours up to 10 hours for example, in order to bring about a reduction of the vanadium pentoxide. Subsequently the 102 to 110% strength phosphoric acid is added, following its possible dilution if desired with a primary or secondary, noncyclic or cyclic, unbranched or branched, saturated alcohol having from 3 to 6 carbon atoms, with further stirring.

In a fourth variant of said combining, the 102 to 110% strength phosphoric acid, which may if desired have been diluted with a primary or secondary, noncyclic or cyclic, unbranched or branched, saturated alcohol having from 3 to 6 carbon atoms, is introduced as an initial charge which is then brought preferably to a temperature of from 50 to 160° C. and with particular preference from 50 to 100° C. This is followed by the introduction of vanadium pentoxide in the form of a solid or, where appropriate, in the form of a suspension in a primary or secondary, noncyclic or cyclic, unbranched or branched, saturated alcohol having from 3 to 6 carbon atoms. The vanadium pentoxide or its suspension may if desired likewise have been conditioned to an elevated temperature, from 50 to 100° C. for example.

In a fifth variant of said combining, the primary or secondary, noncyclic or cyclic, unbranched or branched, saturated alcohol having from 3 to 6 carbon atoms is introduced as an initial charge which is then brought preferably to a temperature of from 50 to 160° C. and with particular preference from 50 to 100° C. This is followed by the introduction of vanadium pentoxide, in the form of a solid or, where appropriate, in the form of a suspension in a primary or secondary, noncyclic or cyclic, unbranched or branched, saturated alcohol having from 3 to 6 carbon atoms, and also of the 102 to 110% strength phosphoric acid, which may where appropriate have been diluted with a primary or secondary, noncyclic or cyclic, unbranched or branched, saturated alcohol having from 3 to 6 carbon atoms, with stirring. The vanadium pentoxide or its suspension may where appropriate again have been conditioned to an elevated temperature, from 50 to 100° C. for example. In order to lower the viscosity of the phosphoric acid for introduction it may be advantageous to condition it to a temperature in the range from 40 to 100° C. The addition of the vanadium pentoxide and of the 102 to 110% strength phosphoric acid may be commenced simultaneously or else with a delay. It is preferred to commence with the addition of vanadium pentoxide and not to introduce the 102 to 110% strength phosphoric acid until the further course of the addition of vanadium pentoxide or else only subsequently.

The relative molar ratio of the 102 to 110% strength phosphoric acid to the vanadium pentoxide is generally set in accordance with the desired ratio in the catalyst precursor. In the reaction mixture for preparing the catalyst precursor, the molar phosphorus/vanadium ratio is preferably from 1.0 to 1.5 and with particular preference from 1.1 to 1.3.

The amount of the primary or secondary, noncyclic or cyclic, unbranched or branched, saturated alcohol having from 3 to 6 carbon atoms should advantageously be beyond the amount required stoichiometrically to reduce the vanadium from oxidation state +5 to an oxidation state in the range from +3.5 to +4.5. The amount should also be such as to be able to form, with the vanadium pentoxide, a suspension which allows intensive mixing with the 102 to 110% strength phosphoric acid. The molar ratio of the alcohol to the vanadium pentoxide is generally from 10 to 25 and preferably from 12 to 20.

When the vanadium pentoxide, 102–110% strength phosphoric acid, and C3–C6 alcohol components have been combined, the reaction of these compounds is accomplished by heating the mixture at a temperature from 80 to 160° C. over a period of usually several hours. The temperature range to be selected is dependent on a variety of factors, one example being the boiling point of the added alcohol, and can be optimized by means of simple experiments. When using isobutanol, which is very particularly preferred, the mixture is heated preferably at a temperature from 90 to 120° C. and with particular preference from 100 to 110° C. The volatile compounds, such as water, the alcohol and its degradation products, such as aldehyde or carboxylic acid, for instance, evaporate from the reaction mixture and can either be taken off or else completely or partly condensed and recycled. Preference is given to complete or partial recycling by heating under reflux. Complete recycling is particularly preferred. The reaction at elevated temperature generally lasts several hours and is dependent on a large number of factors, such as the nature of the added components or the temperature, for example. Moreover, within a certain range, the temperature and the selected heating period may also be used to set and influence the properties of the catalyst precursor. For a given system, the parameters of temperature and time can be optimized simply by means of a few experiments. The time taken for said reaction is customarily from 1 to 25 hours.

Step (b)

After the end of the reaction, the precipitate formed is isolated, where appropriate following a cooling phase and also a storage or aging phase of the cooled reaction mixture. In the isolation procedure, the precipitate is separated off from the liquid phase. Examples of suitable methods are filtration, decanting, and centrifugation. The precipitate is preferably isolated by filtering or centrifuging. Isolation of the precipitate takes place generally likewise within a temperature range from 0 to 160° C., with temperatures in the range from 50 to 150° C., in particular from 80 to 150° C., being preferred.

The isolated precipitate can be processed further with or without washing. Washing the isolated precipitate has the advantage that adhering residues of the alkanol and its degradation products can be reduced further in amount. Examples that may be given of suitable solvents for the washing operation include alcohols (e.g., methanol, ethanol, 1-propanol, 2-propanol, and the primary or secondary, noncyclic or cyclic, unbranched or branched, saturated alcohol having from 3 to 6 carbon atoms that was selected for the preceding reaction), aliphatic and/or aromatic hydrocarbons (e.g., pentane, hexane, petroleum spirits, benzene, toluene, xylenes), ketones (e.g., 2-propanone (acetone), 2-butanone, 3-pentanone, ethers (e.g., 1,2-dimethoxyethane, tetrahydrofuran, 1,4-dioxane) or mixtures thereof. Where the isolated precipitate is washed, it is preferred to use the primary or secondary, noncyclic or cyclic, unbranched or branched, saturated alcohol having from 3 to 6 carbon atoms that was selected for the preceding reaction.

The isolated precipitate can be processed further with or without drying. In general, the isolated precipitate is dried. Drying can be conducted under a variety of conditions. It is generally conducted at a pressure of from 0.0 ("vacuum") to 0.1 MPa abs ("atmospheric pressure"). The drying temperature is generally from 30 to 250° C., although in many cases it is possible to employ lower temperatures when drying under vacuum than when drying under atmospheric pressure. The gas atmosphere over the products, where appropriate, during drying may comprise oxygen, steam and/or inert gases, such as nitrogen, carbon dioxide or noble gases. Drying is preferably conducted under a pressure of from 1 to 30 kPa abs at a temperature of from 50 to 200° C. under an oxygenous or oxygen-free residual gas atmosphere, such as air or nitrogen, for example.

Drying can be carried out, for example, in the filtration device itself or in a separate apparatus, a drying oven or a continuous belt dryer, for example.

Step (c)

In step (c), an organic carbon content of $\leq 1.1\%$ by weight is set in the isolated precipitate by heat treatment in a temperature range from 250 to 350° C., the heat-treated product, following the addition of 3.0% by weight of graphite as internal standard and using CuK$\alpha$ radiation ($\lambda=1.54\cdot10^{-10}$ m), giving a powder X-ray diffraction diagram which in the 2θ region features a ratio of the height of the peak of any pyrophosphate phase present at 28.5° to the height of the peak due to the graphite at 26.6° of $\leq 0.1$.

Organic carbon here is any carbon which cannot be expelled from the powderous sample by adding 10% strength by weight aqueous hydrochloric acid and then heating the mixture while passing a stream of nitrogen through it. The organic carbon content is calculated from the difference between the total carbon content and the inorganic carbon content.

In order to determine the total carbon content, a powderous sample of known, precise weight is introduced in the presence of a stream of pure oxygen into a quartz tube heated at about 1000° C., the sample is calcined, and the carbon dioxide present in the combustion gas is quantified. By working back from the amount of carbon dioxide detected and the initial mass of the sample, it is then possible to determine the total carbon content. A precise description of the method is given in the examples under "Determination of the total carbon content".

In order to determine the inorganic carbon content, a powderous sample of known, precise weight is admixed with 10% strength by weight aqueous hydrochloric acid, the carbon dioxide evolved is expelled by slow heating while passing a stream of nitrogen through it, and the expelled carbon dioxide is quantified. By working back from the amount of carbon dioxide detected and the initial sample mass, it is then possible to calculate the inorganic carbon content. A precise description of the method is given in the examples under "Determination of the inorganic carbon content".

In the process of the invention, the heat treatment of step (c) is used to set an organic carbon content of preferably $\leq 1.0\%$ by weight, with particular preference $\leq 0.8\%$ by weight, and with very particular preference $\leq 0.7\%$ by weight.

The total carbon content is generally $\leq 2.0\%$ by weight, preferably $\leq 1.5\%$ by weight, and with particular preference $\leq 1.2\%$ by weight.

The inventive measure of setting a low organic carbon content of $\leq 1.1\%$ by weight minimizes or prevents damage to the catalyst during the subsequent calcining of the particulate catalyst precursor and also allows a very uniform oxidation state of the vanadium to be set throughout the catalyst molding. At higher organic carbon contents, i.e., at levels above 1.1% by weight, there is a risk of sustained mechanical and/or chemical damage due to a sharp local increase in pressure as a result of volatilization, decomposition and/or oxidation of the organic compounds, to local hot spots as a result of a chemical reaction of the organic compounds with the catalyst material and/or with the gas phase (e.g., oxidation by oxygen), and to local reduction of the catalyst material as a result of a chemical reaction between the reductive organic compounds and the catalyst material. The last-mentioned local reduction of the catalyst material at organic carbon contents above 1.1% by weight leads to a very non uniform oxidation state of the vanadium over the catalyst molding, with the inlying regions having a much lower vanadium oxidation state than the outlying regions.

As already mentioned, the heat treatment in step (c) is carried out such that following the addition of 3.0% by weight of graphite as internal standard and using CuKα radiation ($\lambda=1.54\cdot 10^{-10}$ m) the heat-treated product gives a powder X-ray diffraction diagram which in the 2θ region features a ratio of the height of the peak of any pyrophosphate phase present at 28.5° to the height of the peak due to the graphite at 26.6° of $\leq 0.1$.

The X-ray diffraction (XRD) diagram shows the intensity of the diffracted X-rays (in counts per second, cps) as a function of twice the diffraction angle, 2θ. The powder XRD diagram is recorded using the powderous precipitate intimately mixed with 3% by weight of graphite. Recording takes place with a powder diffractometer with adjustable aperture and collimator, measurements being made in reflexion. Each peak height is a product of the difference between the maximum intensity of the respective signal and the measured background. A precise description of the method is given in the examples under "X-ray-diffractometric analysis of the heat-treated precipitate".

In the process of the invention, the heat treatment in step (c) is carried out such that following the addition of 3.0% by weight of graphite as internal standard and using CuKα radiation ($\lambda=1.54\cdot 10^{-10}$ m) the heat-treated product gives a powder X-ray diffraction diagram which in the 2θ region features a ratio of the height of the peak any pyrophosphate phase present at 28.5° to the height of the peak due to the graphite at 26.6° of preferably $\leq 0.08$, with particular preference $\leq 0.05$, and with very particular reference $\leq 0.02$.

In the process of the invention, the heat treatment in step (c) takes place within a temperature range from 250 to 350° C., preferably from 260 to 350° C., and with particular preference from 270 to 340° C. Heat treatment may in principle be carried out within a wide pressure range, the use of low pressures generally promoting the removal of organic components. Generally speaking, the heat treatment is conducted under a pressure from 0.0 ("vacuum") to 0.15 MPa abs, preferably at approximately 0.1 MPa abs ("atmospheric pressure").

Heat treatment generally occupies a time ranging from several minutes to several hours and is dependent on a large number of factors, such as, for example, the concentration of the phosphoric acid used, the nature of the primary or secondary, noncyclic or cyclic, unbranched or branched, saturated alcohol having from 3 to 6 carbon atoms that is used, the further treatment of the deposited precipitate (e.g., aging of the precipitate), and the selected heat treatment temperature. For example, it is possible for a lengthy heat treatment at a low temperature to give a result similar to that of a shorter heat treatment at a moderate or higher temperature. For a given system, the parameters of temperature and time can be optimized simply by means of a few experiments. In general, the necessary heat treatment time is from 0.5 to 10 hours.

The gas atmosphere during heat treatment may comprise oxygen, steam and/or inert gases, such as nitrogen, carbon dioxide or noble gases. Preferably, heat treatment takes place in air.

The heat treatment can be operated batchwise or continuously, for example. Suitable apparatus includes ovens, muffle furnaces, belt calcining means, fluid-bed dryers, and rotary tubes. In order to give a uniformly heat-treated product it is generally advantageous to use a continuously operating heat treatment process with mixing of the powder to be heat-treated. Particular preference is therefore given to heat treatment in a continuously operated rotary tube.

Step (d)

In step (d), the heat-treated product obtained from step (c) is shaped into particles having an averaged diameter of at least 2 mm and preferably of at least 3 mm. The averaged diameter of a particle is the mean of the smallest and largest dimensions between two plane-parallel plates.

By particles are meant both irregularly shaped particles and geometrically shaped particles, referred to as moldings. The heat-treated product obtained from step (c) is preferably shaped into moldings. Examples of suitable moldings include tablets, cylinders, hollow cylinders, beads, strands, wagon wheels, and extrudates. Special shapes, such as trilobes and tristars (see WO 93/01155) or moldings with at least one notch on the outside (see U.S. Pat. No. 5,168,090), are likewise possible.

Where the shaping of the heat-treated product takes place by tableting, as is customary, for example, in the production of tablets, cylinders, and hollow cylinders, it is normal to add a tableting aid to the powder and to intimately mix the two components. Tableting aids are generally catalytically inert and enhance the tableting properties of the powder, by increasing the sliding properties and free-flow properties, for example. One suitable, preferred tableting aid is graphite. The added tableting aids generally remain within the activated catalyst. The amount of tableting aid in the finished catalyst is typically from about 2 to 6% by weight.

Particular preference is given to shaping moldings having a substantially hollow cylindrical structure. A substantially hollow cylindrical structure is a structure which substantially embraces a cylinder having a continuous aperture between the two end faces. The cylinder is characterized by two substantially parallel end faces and a lateral surface, the cross section of the cylinder, i.e., parallel to the end faces, being substantially of circular structure. The cross section of the continuous aperture, i.e., parallel to the end faces of the cylinder, is likewise substantially of circular structure. The continuous aperture is preferably located centrally with respect to the end faces, although this is not to exclude other spatial arrangements.

The phrase "substantially" indicates that deviations from the ideal geometry, such as slight deformations in the circular structure, end faces which are not in plane-parallel alignment, flaked-off angles and edges, surface roughness or notches in the lateral surface, in the end faces, or in the inner surface of the continuous hole, for example, are included in the catalyst of the invention. Within the bounds of the accuracy of the tableting art, circular end faces, a circular cross section of the continuous hole, end faces in parallel alignment, and macroscopically smooth surfaces are preferred.

The substantially hollow cylindrical structure can be described by an external diameter $d_1$, a height h, as the distance between the two end faces, and an inner-hole (continuous-aperture) diameter $d_2$. The external diameter $d_1$ is preferably from 3 to 10 mm, with particular preference from 4 to 8 mm, with very particular preference from 4.5 to 6 mm. The height h is preferably from 1 to 10 mm, with particular preference from 2 to 6 mm, with very particular preference from 2 to 3.5 mm. The continuous-aperture diameter $d_2$ is preferably from 1 to 8 mm, with particular preference from 2 to 6 mm, with very particular preference from 2 to 3 mm. Particular preference is given to a hollow cylindrical structure which features (a) a ratio of the height h to the continuous-aperture diameter $d_2$ of not more than 1.5 and (b) a ratio of the geometric surface area $A_{geo}$ to the geometric volume $V_{geo}$ of at least 2 $mm^{-1}$, as is described, for instance, in WO 01/68245.

The substantial to complete avoidance of the formation of the pyrophosphate phase in the heat-treated precipitate in step (c) and the shaping in step (d) prior to actual calcination, i.e., the conversion of the vanadyl hydrogen phosphate hemihydrate phase ($VOHPO_4 \cdot \frac{1}{2} H_2O$) into the catalytically active pyrophosphate phase (($VO)_2P_2O_7$), with elimination of water, surprisingly gives a catalyst structure which is more advantageous as far as the catalytic properties are concerned than in the case of shaping carried out after said phase conversion.

In one particularly preferred embodiment for the preparation of the catalyst precursor, a suitable stirred apparatus is charged with a suspension of vanadium pentoxide in isobutanol, this initial charge is heated to a temperature in the range from 50 to 100° C., and phosphoric acid with a strength of from 102 to 110% is introduced with further stirring. The mixture is stirred further for several hours with heating at a temperature in the range from 100 to 110° C. under reflux. Thereafter the hot suspension is filtered and the solid product is washed with a little isobutanol and dried under reduced pressure at a temperature in the range from 100 to 200° C. The isolated and dried precipitate is then subjected to continuous heat treatment, preferably in a rotary tube, in air at approximately atmospheric pressure, in a temperature range from 250 to 350° C. and with an average residence time in the range from 0.5 to 5 hours, preferably from 1 to 3 hours. The heat treatment conditions are selected such that the heat-treated product possesses an organic carbon content of ≦1.1% by weight and, following the addition of 3.0% by weight of graphite as internal standard and using CuKα radiation ($\lambda=1.54 \cdot 10^{-10}$ m), gives a powder X-ray diffraction diagram which in the 2θ region features a ratio of the height of the peak of any pyrophosphate phase present at 28.5° to the height of the peak due to the graphite at 26.6° of ≦0.1. The heat-treated product obtained is then intimately mixed with from 2 to 6% by weight of graphite and the mixture is tableted to give moldings in the form of tablets or hollow cylinders. The catalyst precursor is preferably tableted to hollow cylinders having an external diameter $d_1$ of from 4.5 to 6 mm, a height h of from 2 to 3.5 mm, and a continuous-aperture diameter $d_2$ of from 2 to 3 mm.

BRIEF DESCRIPTION OF THE FIGURES:

FIG. 1 is a background-corrected XRD diagram of a representative sample of the catalyst precursor from example 2.2, heat-treated in the muffle furnace, following addition of 3.0% by weight of graphite.

FIG. 2 is a light micrograph of the catalyst from example 2.1 heat-treated in the muffle furnace at 250° C. and then tableted and calcined (comparative example). The duplicate arrow signifying "V-Ox =3,97"is provided merely to clarify the difficult to read white text and white arrow, which were originally placed overtop of the light micrograph.

FIG. 3 is a light micrograph of the catalyst from example 2.2 heat-treated in the muffle furnace at 300° C. and then tableted and calcined.

FIG. 4. is a background-corrected XRD diagram of a representative sample of the catalyst precursor from example 4.4, heat-treated in the rotary tube, following addition of 3.0% by weight of graphite.

FIG. 5 is an XRD diagram of the catalyst precursor from example 6, heat-treated at 400° C., following addition of 3.0% by weight of graphite.

The invention further provides a catalyst precursor for preparing maleic anhydride by heterogeneously catalyzed gas-phase oxidation of a hydrocarbon having at least four carbon atoms, said precursor being obtainable by the process of the invention described above.

The process of the invention makes it possible to prepare a vanadium, phosphorus, and oxygen catalyst precursor for preparing maleic anhydride by heterogeneously catalyzed gas-phase oxidation of a hydrocarbon having at least four carbon atoms, the catalyst precursor being easy to prepare industrially and having a particularly low organic carbon content and, as a selectivity-defining and activity-defining precursor, allowing the preparation of a catalyst which features high activity and high selectivity.

The invention further provides a process for preparing a vanadium-phosphorus-oxygen catalyst for preparing maleic anhydride by heterogeneously catalyzed gas-phase oxidation of a hydrocarbon having at least four carbon atoms by treating a vanadium, phosphorus, and oxygen catalyst precursor in at least one atmosphere comprising oxygen ($O_2$), hydrogen oxide ($H_2O$), and/or inert gas in a temperature range from 250 to 600° C., which comprises using as catalyst precursor a catalyst precursor of the invention as described above.

Examples of suitable inert gases that may be mentioned include nitrogen, carbon dioxide, and noble gases.

Calcination can be carried out batchwise, in a shaft furnace, tray furnace, muffle furnace or oven, for example, or continuously, in a rotary tube, belt kiln or rotary sphere kiln, for example. It may comprise successive, different sections as far as temperature is concerned, such as heating, temperature hold, or cooling, and successive, different sections as far as the atmospheres are concerned, such as oxygenous, steam-containing or oxygen-free gas atmospheres. Suitable preactivation processes are described, for example, in patents U.S. Pat. Nos. 5,137,860 and 4,933,312 and in the OPI document WO 95/29006, which are expressly hereby incorporated but without limitation. Particular preference is given to continuous calcination in a belt kiln having at least two—for example, from two to ten—calcining zones, where appropriate with different gas atmospheres and different temperatures. By means of an appropriate combination of temperatures, treatment times, and gas atmospheres, adapted to the respective catalyst system, it is possible to influence and hence to tailor the mechanical and catalytic property of the catalyst.

Preferred in the process of the invention is a calcination wherein the catalyst precursor (i) is heated to a temperature from 200 to 350° C. in at least one calcining zone in an oxidizing atmosphere having an oxygen content of from 2 to 21% by volume and is left under these conditions until the vanadium has the desired average oxidation state; and (ii) is heated to a temperature from 300 to 500° C. in at least one further calcining zone in a non oxidizing atmosphere having an oxygen content of $\leq 0.5\%$ by volume and a hydrogen oxide content of from 20 to 75% by volume, and is left under these conditions for $\geq 0.5$ hour.

In step (i), the catalyst precursor is left in an oxidizing atmosphere having a molecular oxygen content of generally from 2 to 21% by volume and preferably from 5 to 21% by volume at a temperature from 200 to 350° C. and preferably from 250 to 350° C. for a period effective to set the desired average oxidation state of the vanadium. Step (i) generally employs mixtures of oxygen, inert gases (e.g., nitrogen or argon), hydrogen oxide (steam) and/or air, and also air itself. From the standpoint of the catalyst precursor which is passed through the calcining zone or zones, the temperature during calcining step (i) may be kept constant or may on average rise or fall. Since step (i) is generally preceded by a heating phase, the temperature will generally rise first of all before then leveling off at the desired end value. In general terms, therefore, the calcining zone of step (i) is preceded by at least one further calcining zone in which the catalyst precursor is heated.

The time for which the heat treatment in step (i) is maintained is preferably selected, in the process of the invention, so as to set an average vanadium oxidation state at a value of from +3.9 to +4.4, preferably from +4.0 to +4.3. The average oxidation state of the vanadium is determined by potentiometric titration in accordance with the method described in the examples.

Since for reasons associated with the apparatus and with time it is extremely difficult to determine the average oxidation state of the vanadium during the calcining operation, the time period required is advantageously determined in preliminary experiments. This purpose is typically served by a series of measurements wherein heat treatment is carried out under defined conditions, with the samples being removed from the system after different times, cooled, and analyzed for the average oxidation state of the vanadium.

The time period required in the case of step (i) is generally dependent on the nature of the catalyst precursor, on the set temperature, and on the selected gas atmosphere, particularly on the oxygen content. Generally speaking, the time period for step (i) extends to a duration of more than 0.5 hour and preferably of more than 1 hour. A period of up to 4 hours, preferably of up to 2 hours, is generally sufficient to set the desired average oxidation state. Under appropriately adjusted conditions (e.g., lower range of the temperature span and/or low molecular oxygen content), however, a period of more than 6 hours may also be necessary.

In step (ii), the resultant catalyst intermediate is left in a non oxidizing atmosphere having a molecular oxygen content of $\leq 0.5\%$ by volume and a hydrogen oxide (steam) content of from 20 to 75% by volume, preferably from 30 to 60% by volume, at a temperature from 300 to 500° C. and preferably from 350 to 450° C. for a period of $\geq 0.5$ hour, preferably from 2 to 10 hours, and with particular preference from 2 to 4 hours. In addition to the hydrogen oxide stated, the non oxidizing atmosphere generally comprises predominantly nitrogen and/or noble gases, such as argon, for example, but without this constituting any restriction. Gases such as carbon dioxide, for example, are also suitable in principle. The non oxidizing atmosphere preferably comprises $\geq 40\%$ by volume of nitrogen. From the standpoint of the catalyst precursor which is passed through the calcining zone or zones, the temperature during calcining step (ii) may be held constant or may on average rise or fall. Where step (ii) is conducted at a higher or lower temperature than step (i), there is typically a heating or cooling phase between steps (i) and (ii) which is implemented where appropriate in a further calcining zone. In order to allow improved separation from the oxygenous atmosphere of step (i), said further calcining zone between (i) and (ii) may be flushed with inert gas, such as nitrogen, for example. Step (ii) is preferably conducted at a temperature which is higher by from 50 to 150° C. than that of step (i).

Generally speaking, calcination comprises a further step (iii), to be carried out later than step (ii), wherein the calcined catalyst precursor is cooled under an inert gas atmosphere to a temperature of $\leq 300°$ C., preferably $\leq 200°$ C., and with particular preference $\leq 150°$ C.

Before, between and/or after steps (i) and (ii), or (i), (ii), and (iii), further steps are possible when calcining in accordance with the process of the invention. Without limitation, further steps that may be mentioned include, for example, changes in temperature (heating, cooling), changes in the gas atmosphere (changeover of gas atmosphere), further holding times, transfers of the catalyst intermediate to different apparatus, or interruptions to the overall calcining operation.

Since the catalyst precursor generally has a temperature of <100° C. before calcination begins, it must normally be heated prior to step (i). Heating can be carried out using different gas atmospheres. Heating is preferably conducted in an oxidizing atmosphere, as defined under step (i), or in an inert gas atmosphere, as defined under step (iii). A change in gas atmosphere during the heating phase is also possible. Particular preference is given to heating in the oxidizing atmosphere which is also employed in step (i).

The invention further provides a catalyst for preparing maleic anhydride by heterogeneously catalyzed gas-phase oxidation of a hydrocarbon having at least four carbon atoms, said catalyst being obtainable by the process of the invention described above.

The catalyst prepared preferably by the process of the invention features a phosphorus/vanadium atomic ratio of from 0.9 to 1.5, with particular preference from 0.9 to 1.2, and with very particular preference from 1.0 to 1.1, an average vanadium oxidation state of from +3.9 to +4.4 and with particular preference from 4.0 to 4.3, a BET surface area of from 10 to 50 m²/g and with particular preference from 20 to 40 m²/g, a pore volume of from 0.1 to 0.5 ml/g and with particular preference from 0.2 to 0.4 ml/g, and a bulk density of from 0.5 to 1.5 kg/l and with particular preference from 0.5 to 1.0 kg/l.

The catalyst obtainable by calcining the catalyst precursor of the invention is distinguished by a substantially homogeneous oxidation state of the vanadium within the individual catalyst particles and between the different catalyst particles. In the heterogeneously catalyzed gas-phase oxidation of a hydrocarbon having at least four carbon atoms to maleic anhydride, the catalyst of the invention allows a high hydrocarbon space velocity in combination with high conversion, high activity, high selectivity, and a high space-time yield.

The invention additionally provides a process for preparing maleic anhydride by heterogeneously catalyzed gas-phase oxidation of a hydrocarbon having at least four carbon atoms with oxygenous gases, which comprises using a catalyst of the invention as described above.

In the process of the invention for preparing maleic anhydride, the reactors used are generally shell and tube reactors. Suitable hydrocarbons are generally aliphatic and aromatic, saturated and unsaturated hydrocarbons having at least four carbon atoms, such as 1,3-butadiene 1-butene, 2-cis-butene, 2-trans-butene, n-butane, $C_4$ mixture, 1,3-pentadiene, 1,4-pentadiene, 1-pentene, 2-cis-pentene, 2-trans-pentene, n-pentane, cyclopentadiene, dicyclopentadiene, cyclopentene, cyclopentane, $C_5$ mixture, hexenes, hexanes, cyclohexane, and benzene, for example. Used with preference are 1-butene, 2-cis-butene, 2-trans-butene, n-butane, benzene or mixtures thereof. Particular preference is given to using n-butane and liquids and gases containing n-butane. The n-butane used may come, for example, from natural gas, from steam crackers or from FCC crackers.

The addition of the hydrocarbon generally takes place under flow control, i.e., with continuous introduction of a defined amount per unit time. The hydrocarbon can be metered in liquid or gaseous form. It is preferably metered in liquid form with subsequent vaporization before entering the shell and tube reactor.

Oxidants used are oxygenous gases, such as air, synthetic air, an oxygen-enriched gas, or else what is termed "pure" oxygen, i.e., oxygen originating, for example, from the fractionation of air. The oxygenous gas as well is added under flow control.

The gas to be passed through the shell and tube reactor generally contains a hydrocarbon concentration of from 0.5 to 15% by volume and an oxygen concentration of from 8 to 25% by volume. The remaining fraction is composed of other gases such as nitrogen, noble gases, carbon monoxide, carbon dioxide, steam, oxygenated hydrocarbons (e.g., methanol, formaldehyde, formic acid, ethanol, acetaldehyde, acetic acid, propanol, propionaldehyde, propionic acid, acrolein, and crotonaldehyde) and mixtures thereof. As a proportion of the total amount of hydrocarbon, the n-butane fraction is preferably $\geq 90\%$ and with particular preference $\geq 95\%$.

In order to ensure a long catalyst life and a further increase in conversion, selectivity, yield, space velocity over the catalyst and space-time yield, in the process of the invention it is preferred to supply a volatile phosphorus compound to the gas.

The concentration of this compound at the beginning, i.e., at the reactor entry, is at least 0.2 ppm by volume, i.e., $0.2 \cdot 10^{-6}$ parts by volume of the volatile phosphorus compounds relative to the total volume of the gas at the reactor entry. Preference is given to an amount of from 0.2 to 20 ppm by volume, with particular preference from 0.5 to 10 ppm by volume. Volatile phosphorus compounds are all phosphorus compounds which are present in gaseous form at the desired concentration under the conditions in which they are used. Examples of suitable volatile phosphorus compounds include phosphines and phosphates. Particular preference is given to the $C_1$ to $C_4$ alkyl phosphates, with very particular preference trimethyl phosphate, triethyl phosphate, and tripropyl phosphate, and especially triethyl phosphate.

The process of the invention is generally conducted at a temperature from 350 to 480° C. The temperature referred to here is the temperature of the catalyst bed in the shell and tube reactor which said bed would be at were the process to be performed in the absence of a chemical reaction. If this temperature is not exactly the same at every point, then the term refers to the numerical average of the temperatures along the reaction zone. This means in particular that the true temperature prevailing at the catalyst may even lie outside of the stated range, owing to the exothermic nature of the oxidation reaction. The process of the invention is preferably conducted at a temperature from 380 to 460° C., with particular preference from 380 to 430° C.

The process of the invention can be performed at a pressure below atmospheric pressure (e.g., up to 0.05 MPa abs) or else above atmospheric pressure (e.g., up to 10 MPa abs). The pressure referred to here is the pressure within the shell and tube reactor unit. A pressure of from 0.1 to 1.0 MPa abs is preferred, with particular preference from 0.1 to 0.5 MPa abs.

The process of the invention can be carried out in two preferred modes, the straight pass mode and the recirculation mode. In the straight pass mode, maleic anhydride and any oxygenated hydrocarbon byproducts are subtracted from the reactor discharge and the remaining gas mixture is removed and employed where appropriate for generating heat. In the case of the recirculation mode, maleic anhydride and any oxygenated hydrocarbon byproducts are again subtracted from the reactor discharge but some or all of the remaining gas mixture, which contains unreacted hydrocarbon, is recycled to the reactor. Another variant of the recirculation mode involves removing the unreacted hydrocarbon and recycling it to the reactor.

In one particularly preferred embodiment for the preparation of maleic anhydride, n-butane is the starting hydrocarbon used and the heterogeneously catalyzed gas-phase oxidation is conducted in a straight pass over the catalyst of the invention.

The process of the invention using the catalysts of the invention allows a high hydrocarbon space velocity of the catalyst in combination with a high conversion rate owing to a high activity. The process of the invention also permits high selectivity, a high yield, and hence a high space-time yield of maleic anhydride as well.

Definitions

The variables used in this text, unless specified otherwise, are defined as follows:

$$\text{Space-time yield} = \frac{m_{maleic\ anhydride}}{V_{catalyst} \cdot t}$$

-continued $$\text{Space velocity} = \frac{V_{hydrocarbon}}{V_{catalyst} \cdot t}$$

$$\text{Conversion } U = \frac{n_{HC,reactor,in} - n_{HC,reactor,out}}{n_{HC,reactor,in}}$$

$$\text{Selectivity } S = \frac{n_{MAN,reactor,out}}{n_{HC,reactor,in} - n_{HC,reactor,out}}$$

$$\text{Yield } A = U \cdot S$$

$m_{maleic\ anhydride}$ Mass of maleic anhydride produced [g]

$V_{catalyst}$ Bulk volume of catalyst summated over all reaction zones [L]

t Time unit [h]

$V_{hydrocarbon}$ volume of hydrocarbon in the gas phase, standardized to 0° C. and 0.1013 MPa [L(stp)] (Arithmetic variable. Where a hydrocarbon is in the liquid phase under these conditions, the hypothetical gas volume is calculated using the ideal gas law.)

U Conversion of hydrocarbons per reactor pass

S Selectivity for maleic anhydride per reactor pass

A Yield of maleic anhydride per reactor pass $n_{HC,\ reactor,\ in}$ Volume flow of hydrocarbons at the reactor entry [mol/h]

$n_{HC,\ reactor,\ out}$ Volume flow of hydrocarbons at the reactor exit [mol/h]

$n_{HC,\ plant,\ in}$ Volume flow of hydrocarbons at the plant entry [mol/h]

$n_{HC,\ plant,\ out}$ Volume flow of hydrocarbons at the plant exit [mol/h]

$n_{MAN,\ reactor,\ out}$ Volume flow of maleic anhydride at the reactor exit [mol/h]

$n_{MAN,\ plant,\ out}$ Volume flow of maleic anhydride at the plant exit [mol/h]

EXAMPLES

Determination of the Residual Isobutanol Content of the Dried Catalyst Precursor In order to determine the residual isobutanol content, about 4 g of the dried powderous catalyst precursor and about 10 g of N,N-dimethylformamide were weighed out precisely into a heatable stirred apparatus with reflux condenser. The mixture was then heated to boiling temperature with stirring and left under these conditions for 30 minutes. After cooling, the suspension was filtered and the isobutanol content of the filtrate was quantified by gas chromatography. The residual isobutanol content was then calculated from the concentration of isobutanol found in the N,N-dimethylformamide and from the initial weights of N,N-dimethylformamide and catalyst precursor.

Determination of the Total Carbon Content

In order to determine the total carbon content, approximately 50 to 200 mg of the powderous sample, weighed out precisely, were introduced in the presence of a stream of pure oxygen into a quartz tube heated to about 1000° C., and calcined. The combustion gas obtained was passed through an IR cell and the carbon dioxide content was quantified. Working back from the amount of carbon dioxide detected, it was possible to calculate the total carbon content of the sample.

Determination of the Inorganic Carbon Content

In order to determine the inorganic carbon content, about 50 to 200 mg of the powderous sample, weighed out precisely, were admixed with 10% strength by weight aqueous hydrochloric acid.

The carbon dioxide evolved was expelled with slow heating, during which a stream of nitrogen was passed through the mixture, and was purified by passing it through a cascade comprising a cold trap cooled with isopropanol/dry ice, two absorption vessels containing potassium permanganate solution, one absorption vessel containing concentrated sulfuric acid, and a manganese dioxide tube. The purified stream of gas was passed into a coulometer cell which was filled with a solution of 0.1% by weight thymolphthalein in dimethyl sulfoxide, and the change in color was monitored photometrically. From the change in transmission it is possible to deduce the amount of carbon dioxide introduced and hence the inorganic carbon content of the sample.

Determination of the Organic Carbon Content

The organic carbon content is calculated from the difference between the total carbon content and the inorganic carbon content.

X-ray-diffractometric Analysis of the Heat-treated Precipitate

For XRD analysis, the powderous precipitate intimately mixed with 3% by weight of graphite was subjected to measurement in a Siemens D5000 theta/theta X-ray powder diffractometer. The measurement parameters were as follows:

| | |
|---|---|
| Circle diameter | 435 mm |
| X-rays | CuKα (λ = 1.54 · 10$^{-10}$ m) |
| Tube voltage | 40 kV |
| Tube current | 30 mA |
| Aperture | variable V20 |
| Collimator | variable V20 |
| Secondary monochromator | Graphite |
| Monochromator aperture | 0.1 mm |
| Detector aperture of scintillation counter | 0.6 mm |
| Step | 0.02° 2θ |
| Step mode | continuous |
| Measurement time | 2.4 s/step |
| Measurement rate | 0.5° 2θ/min |

Each peak height is given by the difference between the maximum intensity of the respective signal and the measured background.

Determination of the Lateral Compressive Strength of the Hollow Cylinders

In order to determine the lateral compressive strength, the hollow cylinders were placed in each case by the rounded side face onto the planar metal platform of a corresponding measuring device, in successive measurements. The two plane-parallel end faces were therefore in the vertical direction. A planar metal die was then lowered onto the hollow cylinder at a rate of advance of 1.6 mm/min and the progress of the force acting on the hollow cylinder was recorded until the cylinder fractured. The lateral compressive strength of each individual hollow cylinder corresponds to the maximum force.

The lateral compressive strength was determined by averaging the result of 30 individual measurements.

Determination of the Average Oxidation State of the Vanadium

The average oxidation state of the vanadium was determined by potentiometric titration.

For the determination, from 200 to 300 mg of each sample were introduced under argon into a mixture of 15 mL of 50% strength sulfuric acid and 5 mL of 85% strength phosphoric acid, and dissolved with heating. The solution was subsequently transferred to a titration vessel fitted with two Pt electrodes. Each titration was carried out at 80° C. A titration with 0.1 molar potassium permanganate solution was carried out first. Where there were two steps resulting in the potentiometric curve, the vanadium was present in an average oxidation state of from +3 to less than +4. Where only one step was obtained, the vanadium was in an oxidation state of from +4 to less than +5.

In the first-mentioned case (two steps/+3 ≦ $V_{ox}$ < +4) the solution contained no $V^{5+}$; in other words, all of the vanadium was detected titrimetrically. The amount of $V^{3+}$ and $V^{4+}$ was calculated from the consumption of 0.1 molar potassium permanganate solution and the position of the two steps. The weighted average then gave the average oxidation state.

In the second-mentioned case (one step/+4 ≦ $V_{ox}$ < +5), the amount of $V^{4+}$ was calculated from the consumption of 0.1 molar potassium permanganate solution. By then reducing the total $V^{5+}$ in the resulting solution with a 0.1 molar ammonium iron(II) sulfate solution and carrying out oxidation again with 0.1 molar potassium permanganate solution, the total amount of vanadium was calculated. The difference between the total amount of vanadium and the amount of $V^{4+}$ gave the amount of $V^{5+}$ originally present.

The weighted average then gave the average oxidation state.

Experimental Plant

The experimental plant was equipped with a feed unit and a reactor tube. Replacing a shell and tube reactor by a reactor tube is entirely valid on the laboratory or pilot plant scale provided the dimensions of the reactor tube are within the range of an industrial reactor tube. The plant was operated in straight pass mode.

The hydrocarbon was added in liquid form under flow control via a pump. Air was added, under flow control, as the oxygenous gas. Triethyl phosphate (TEP) was added in liquid form, in solution in water, again under flow control.

The shell and tube reactor unit consisted of a shell and tube reactor having one reactor tube. The length of the reactor tube was 6.5 m and its internal diameter was 22.3 mm. Within the reactor tube, a tube with an external diameter of 6 mm protected a multiple thermocouple having 20 temperature measurement points. The reactor tube was surrounded by a thermostatable circuit of heat transfer medium and was traversed from top to bottom by the reaction gas mixture. The upper 0.3 m of the reactor tube was filled with inert material and formed the preheating zone. The reaction zone contained 2.2 l of each catalyst. The heat transfer medium used was a salt melt.

Directly downstream of the shell and tube reactor unit, gaseous product was subtracted and supplied to the gas chromatograph for on-line analysis. The main stream of the gaseous reactor discharge was separated from the plant.

The plant was operated as follows:
n-Butane concentration at the reactor entry=2.0% by volume
WHSV=2 000 L(stp)/$L_{catalyst}$·h
Pressure at the reactor exit=0.2 MPa abs
Concentration of triethyl phosphate (TEP)=2 ppm by volume
Concentration of steam=1.5% by volume Example 1

Preparation of the Dried Catalyst Precursor on the Industrial Scale

An 8 m³ steel/enamel stirred tank, rendered inert with nitrogen, externally heatable by way of pressurized water, and containing flow breakers was charged with 6.1 m³ of isobutanol. After the three-stage impeller stirrer had been started up, the isobutanol was heated to 90° C. under reflux. On reaching this temperature, the addition of 736 kg of vanadium pentoxide was commenced by way of the conveying screw. When, after about 20 minutes, about ⅔ of the desired amount of vanadium pentoxide had been added, the addition of vanadium pentoxide was continued accompanied by the pumped introduction of 900 kg of 105% strength phosphoric acid. The pump was cleaned by passing a further 0.2 m³ of isobutanol through it. The reaction mixture was subsequently heated to about 100 to 108° C. under reflux and was left under these conditions for 14 hours. Thereafter the hot suspension was drained off into a pressure suction filter, which had been rendered inert with nitrogen and heated beforehand, and was filtered at a temperature of approximately 100° C. under a pressure above the suction filter of up to 0.35 MPa abs. The filtercake was blown dry by continuous introduction of nitrogen at 100° C., with stirring using a centrally arranged, height-adjustable stirrer, over the course of about one hour. After it had been blown dry, the product was heated to about 155° C. and evacuated to a pressure of 15 kPa abs (150 mbar abs). Drying was carried out to a residual isobutanol content of <2% by weight in the dried catalyst precursor.

In order to produce the desired amount of catalyst precursor, about 9 t, a number of runs were carried out.

Example 2

Heat Treatment, Tableting, and Calcination of the Catalyst Precursor from Example 1 on the Laboratory Scale A sample of about 10 kg of the dried precursor powder obtained in example 1 was taken and in 20 portions each of about 0.5 kg, in succession, was heat-treated in a muffle furnace for 5 hours in air at 250° C. (10 samples, example 2.1) or 300° C. (10 samples, example 2.2). The samples heat-treated at the same temperature were then intimately mixed and the residual isobutanol content, total carbon content, inorganic carbon content, and organic carbon content were determined. In addition, a representative sample from example 2.2 was mixed with 3.0% by weight of graphite and its X-ray diffraction diagram was recorded. This is shown in FIG. 1. The results of the heat-treated catalyst precursor are shown in table 1.

TABLE 1

Analytical data of the catalyst precursor heat-treated in the muffle furnace

|  | Example 2.1* | Example 2.2 |
|---|---|---|
| Heat treatment temperature | 250° C. | 300° C. |
| Residual isobutanol content [% by weight] | 0 | 0 |
| Total carbon content [% by weight] | 1.5 | 0.77 |

TABLE 1-continued

Analytical data of the catalyst precursor heat-
treated in the muffle furnace

|  | Example 2.1* | Example 2.2 |
|---|---|---|
| Inorganic carbon content [% by weight] | 0.15 | 0.35 |
| Organic carbon content [% by weight] | 1.35 | 0.42 |
| XRD peak height ratio I(28.5°)/I(26.6°) | <0.02 | 0.02 |

*Comparative example

The inventive catalyst precursor from example 2.2 has an XRD peak height ratio I(28.5°)/I(26.6°) of 0.02 and an organic carbon content of 0.42% by weight. The catalyst precursor from the comparative example 2.1, on the other hand, has a much higher organic carbon content of 1.35% by weight.

The two heat-treated catalyst precursors were each mixed with 3% by weight of graphite and the mixtures were tabletted in a tableting machine to give hollow cylinders measuring 5×3×2 mm (external diameter×height×inner-hole diameter) having a lateral compressive strength of 20 N. 4.5 kg of each of the two hollow cylinder samples were introduced in succession into a forced air oven and calcined as follows:

Step (1): Heating in air to 250° C. at a rate of 3° C./min.
Step (2): Further heating in air from 250 to 350° C. at a rate of 2° C./min.
Step (3): Holding at this temperature for 15 minutes.
Step (4): Change from air atmosphere to a nitrogen/steam (1:1) atmosphere over 20 minutes.
Step (5): Heating under this atmosphere to 425° C. at a rate of 1.7° C./min.
Step (6): Holding at this temperature for 3 hours.
Step (7): Change of atmosphere to nitrogen, and cooling to room temperature.

The calcined hollow cylinders of the catalysts prepared in accordance with examples 2.1 and 2.2 were investigated for the spatial distribution of the average oxidation state of the vanadium. For this purpose, from a statistically selected amount of the hollow cylinders, a total of about 200 to 300 mg was removed by scratching from the surface (i.e., from the external periphery, from the inner hole, and from the end faces) and used to determine the average oxidation state of the vanadium in the near-surface region. Additionally, a further 200 to 300 mg were isolated mechanically from the inlying area and used to determine the average oxidation state of the vanadium in the inlying area. In addition, the BET surface area was measured. The results obtained are shown in table 2.

TABLE 2

Average oxidation state of the vanadium and BET
surface area of the samples heat-treated differently
in the muffle furnace and then calcined under
identical conditions

|  | Example 2.1* | Example 2.2 |
|---|---|---|
| $V_{ox.}$ (near-surface area) | 4.3 | 4.17 |
| $V_{ox.}$ (inlying area) | 3.97 | 4.17 |
| BET surface area [m²/g] | 20 | 26 |

*Comparative example

As is evident from table 2, the comparative catalyst from example 2.1 shows a significant difference between the average oxidation state of the vanadium in the near-surface area and that in the inlying area. In the near-surface area the average oxidation state is 4.3 and in the inlying area it is 3.97. This significant difference is also evident from the light micrograph, shown in FIG. 2, of a halved hollow cylinder, from the light-colored surface area and the dark inner area. In contrast, the catalyst of the invention from example 2.2 shows a completely uniform distribution of the average vanadium oxidation state of 4.17. The light micrograph of a halved hollow cylinder, shown in FIG. 3, depicts a uniform coloration within the two fracture sites.

Moreover, the BET surface area of the catalyst of the invention from example 2.2, at 26 m²/g, is higher by about 30% (rel.) than that of the comparative catalyst from example 2.1.

Example 3

Catalytic Test of the Catalysts from Example 2

Using in each case 2.2 L of a statistical mixture of the two catalysts from examples 2.1 and 2.2 calcined in the forced air oven, a catalytic performance test was carried out in the experimental plant described above. The salt bath temperature in this case was set so as to give an n-butane conversion of about 84%. The results obtained are shown in table 3.

TABLE 3

Results of the catalytic tests

|  | Catalyst from example 2.1* (heat treatment at 250° C.) | Catalyst from example 2.2 (heat treatment at 300° C.) |
|---|---|---|
| Salt bath temperature [° C.] | 415 | 412 |
| Conversion U [%] | 84.0 | 83.6 |
| Yield A [%] | 50.7 | 55.7 |

*Comparative example

The catalyst prepared in accordance with example 2.2 and heat-treated at 300° C. features virtually the same conversion but a maleic anhydride yield 10% (relative) higher than that of the catalyst prepared in accordance with example 2.1 and heat-treated at 250° C.

Example 4

Heat Treatment of the Catalyst Precursor from Example 1 on the Industrial Scale

Precursor powder prepared in accordance with example 1 was subjected to heat treatment for 2 hours in air in a rotary tube having a length of 6.5 m and an internal diameter of 0.9 m and containing spiral coils. The rotational speed of the rotary tube was 0.4 rpm. The powder was conveyed into the rotary tube at a rate of 60 kg/h. The air supply was 100 m³/h. The temperatures of the five heating zones (which were of equal length), measured directly on the outside of the rotary tube, were 250° C., 300° C., 340° C., 340° C., and 340° C. At statistical intervals, a total of 7 samples of the catalyst precursor heat-treated in the rotary tube were taken, throughout the production process, and the residual isobutanol content, the total carbon content, the inorganic carbon content, and the organic carbon content were determined.

In addition, a representative sample from example 4.4 was mixed with 3.0% by weight of graphite and the X-ray diffraction diagram of the mixture was recorded. The results are shown in table 4 and the X-ray diffraction diagram of example 4.4 is shown in FIG. 4.

As is evident from table 4, all of the analytical data are situated within a very narrow range. No residual isobutanol content was detected in any of the samples. The total carbon content lay within a range from 0.77 to 1.10% by weight, the inorganic carbon content in a range from 0.34 to 0.60% by weight, and the organic carbon content in a range from 0.40 to 0.67% by weight. The XRD peak height ratio I(28.5°)/I(26.6°) of the inventive catalyst precursor from example 4.4 was <0.01.

In addition, the average vanadium oxidation state of the precursor samples was measured. With this analytical value as well, all 7 samples lay within a very narrow range from 4.00 to 4.04.

Example 5

Tableting and Calcination of the Catalyst Precursor from Example 4.5, and Catalytic Test Approximately 4 kg of the heat-treated catalyst precursor from example 4.5 were mixed with graphite as described in example 2, tableted to give hollow cylinders measuring 5×3×2 mm (external diameter×height×internal-hole diameter) and calcined in a forced air oven. 2.2 L of the product were used to carry out a catalytic performance test, as described in example 3, in the experimental plant described above. The salt bath temperature in this case was set so as to give an n-butane conversion of approximately 84%. The results obtained are shown in table 5.

TABLE 5

Results of the catalytic test

|  | Catalyst from example 4.5 |
|---|---|
| Salt bath temperature [° C.] | 410 |
| Conversion U [%] | 84.0 |
| Yield A [%] | 56.0 |

At a salt bath temperature of 410° C. and a conversion rate of 84.0%, the catalyst heat-treated in accordance with example 4.5 gave a maleic anhydride yield of 56.0%. The result obtained is therefore equal to that of the catalyst heat-treated in accordance with example 2.2.

Example 6

Reworking of "Examples 1–7" from EP-A 0 056 183 (Comparative Example)

In example 6, "Examples 1–7" of EP-A 0 056 183 were reworked. For this purpose, 91 g of vanadium pentoxide and 112 g of 105% strength phosphoric acid, corresponding to a composition of about 49% orthophosphoric acid, about 42% pyrophosphoric acid, about 8% triphosphoric acid, and about 1% of higher polyphosphoric acid, were introduced with stirring into 1.5 L of isobutanol and the resulting suspension was heated under reflux for 16 hours. The suspension was subsequently cooled and filtered. The isolated precipitate was dried at 150° C. for 2 hours and heat-treated in air at 400° C. for 1 hour.

The catalyst precursor obtained had a BET surface area of 19 m$^2$/g. The average oxidation state of the vanadium was 4.62. Additionally, a sample was mixed with 3.0% by weight of graphite and the XRD diagram was recorded, this being shown in FIG. 5. The XRD peak height ratio I(28.50)/I(26.6°) obtained was 0.24. From the relatively high XRD peak height ratio it is evident that a significant conversion to vanadium pyrophosphate had already taken place as a result of the heat treatment at 400° C. Moreover, there were unwanted V$^{+5}$OPO$_4$ phases.

Example 7

Reworking of "Example 1, Part A" of EP-A 0 520 972 (Comparative Example)

In example 7, "Example 1, Part A" of EP-A 0 520 972 was reworked. For this purpose, 9 000 mL of isobutanol, 378.3 g of oxalic acid, and 848.4 g of vanadium pentoxide were introduced as an initial charge, 997.6 g of 105.7% strength phosphoric acid were added with stirring, and the suspension obtained was heated under reflux for 16 hours. After about 25% of the isobutanol had been removed by evaporation, over the course of a further hour, the suspension was cooled and about half of the remaining amount of isobutanol was decanted off. The mixture which remained was transferred to a tray and was dried under nitrogen at from 110 to 150° C. for 24 hours. The dried product was subsequently heat-treated in air at from 250 to 260° C. for 5 hours.

The total carbon content of the resulting catalyst precursor was 1.7% by weight, the inorganic carbon content was 0.52% by weight, and the organic carbon content was 1.18% by weight.

As comparative example 7 shows, the catalyst precursor obtained in accordance with the procedure disclosed in EP-A 0 520 972 has an organic carbon content of more than 1.1% by weight.

TABLE 4

Analytical data of the catalyst precursors heat-treated in the rotary tube

| Example | 4.1 | 4.2 | 4.3 | 4.4 | 4.5 | 4.6 | 4.7 |
|---|---|---|---|---|---|---|---|
| Residual isobutanol content [% by weight] | 0 | 0 | 0 | 0 | 0 | 0 | 0 |
| Total carbon content [% by weight] | 1.10 | 1.00 | 0.95 | 1.00 | 0.77 | 1.00 | 1.00 |
| Inorganic carbon content [% by weight] | 0.43 | 0.56 | 0.40 | 0.34 | 0.35 | 0.55 | 0.60 |
| Organic carbon content [% by weight] | 0.67 | 0.44 | 0.55 | 0.66 | 0.42 | 0.45 | 0.40 |
| I(28.5°)/I(26.6°) | n.d. | n.d. | n.d. | <0.01 | n.d. | n.d. | n.d. | n.d.: not determined

We claim:

1. A process for preparing a vanadium, phosphorus, and oxygen catalyst precursor for preparing maleic anhydride by heterogeneously catalyzed gas-phase oxidation of a hydrocarbon having at least four carbon atoms, which comprises
    (a) reacting vanadium pentoxide with from 102 to 110% strength phosphoric acid in the presence of a primary or secondary, noncyclic or cyclic, unbranched or branched, saturated alcohol having from 3 to 6 carbon atoms in a temperature range from 80 to 160° C.;
    (b) isolating the precipitate formed;

(c) setting an organic carbon content of $\leq 1.1\%$ by weight in the isolated precipitate by heat treatment in a temperature range from 250 to 350°, the heat-treated product, following the addition of 3.0% by weight of graphite as internal standard and using CuKα radiation ($\lambda=1.54\cdot10^{-10}$ m), giving a powder X-ray diffraction diagram which in the 2θ region features a ratio of the height of the peak of any pyrophosphate phase present at 28.5° to the height of the peak due to the graphite at 26.6° of $\leq 0.1$; and (d) shaping the heat-treated product obtained from step (c) into particles having an averaged diameter of at least 2 mm.

2. A process as claimed in claim 1, wherein heat treatment in step (c) is conducted at from 270 to 340° C.

3. A process as claimed in claim 1, wherein an organic carbon content of $\leq 0.8\%$ by weight is set in step (c).

4. A process as claimed in claim 1, wherein the heat-treated product from step (c), following the addition of 3.0% by weight of graphite as internal standard and using CuKα radiation ($\lambda=1.54\cdot10^{-10}$ m), gives a powder X-ray diffraction diagram which in the 2θ region features a ratio of the height of the peak of any pyrophosphate phase present at 28.5° to the height of the peak due to the graphite at 26.6° of 0.05.

5. A process as claimed in claim 1, wherein particles of substantially hollow cylindrical structure are shaped in step (d).

6. A process as claimed in claim 1, wherein said primary or secondary, noncyclic or cyclic, unbranched or branched, saturated alcohol having from 3 to 6 carbon atoms is isobutanol.

7. A catalyst precursor for preparing maleic anhydride by heterogeneously catalyzed gas-phase oxidation of a hydrocarbon having at least four carbon atoms, obtainable as claimed in claim 1.

8. A process for preparing a vanadium-phosphorus-oxygen catalyst for preparing maleic anhydride by heterogeneously catalyzed gas-phase oxidation of a hydrocarbon having at least four carbon atoms by treating a vanadium, phosphorus, and oxygen catalyst precursor in at least one atmosphere comprising oxygen ($O_2$), hydrogen oxide ($H_2O$), and/or inert gas in a temperature range from 250 to 600° C., which comprises using a catalyst precursor as claimed in claim 7.

9. A catalyst for preparing maleic anhydride by heterogeneously catalyzed gas-phase oxidation of a hydrocarbon having at least four carbon atoms, obtainable as claimed in claim 8.

10. A process for preparing maleic anhydride by heterogeneously catalyzed gas-phase oxidation of a hydrocarbon having at least four carbon atoms with oxygenous gases, which comprises using a catalyst as claimed in claim 9.

* * * * *

UNITED STATES PATENT AND TRADEMARK OFFICE
CERTIFICATE OF CORRECTION

PATENT NO. : 7,169,732 B2  Page 1 of 1
APPLICATION NO. : 10/507610
DATED : January 30, 2007
INVENTOR(S) : Welguny et al.

It is certified that error appears in the above-identified patent and that said Letters Patent is hereby corrected as shown below:

Column 25, indicated line 24: "of 0.05" should read --of = 0.05--

Signed and Sealed this

Eighteenth Day of September, 2007

JON W. DUDAS
*Director of the United States Patent and Trademark Office*